(12) United States Patent
Thomas et al.

(10) Patent No.: US 7,681,576 B2
(45) Date of Patent: Mar. 23, 2010

(54) MULTIPLE CANNULA SYSTEMS AND METHODS

(75) Inventors: Ralph Thomas, Livermore, CA (US); Luigi Tateo, Byron, CA (US); Duane L. Horton, St. Louis, MO (US); Steven M. Brackney, Livermore, CA (US)

(73) Assignee: Mallinckrodt Inc., St. Louis, MO (US)

( * ) Notice: Subject to any disclaimer, the term of this patent is extended or adjusted under 35 U.S.C. 154(b) by 1821 days.

(21) Appl. No.: 10/429,968

(22) Filed: May 6, 2003

(65) Prior Publication Data

US 2005/0166924 A1  Aug. 4, 2005

(51) Int. Cl.
*A61M 11/00* (2006.01)

(52) U.S. Cl. .......................... 128/207.29; 128/207.14; 128/207.15

(58) Field of Classification Search ............ 128/200.26, 128/202.27, 207.14, 204.18, 207.15, 207.17
See application file for complete search history.

(56) References Cited

U.S. PATENT DOCUMENTS

| | | | |
|---|---|---|---|
| 3,659,612 A * | 5/1972 | Shiley et al. ........... 128/207.15 |
| 3,693,624 A | 9/1972 | Shiley | |
| 4,074,714 A | 2/1978 | Binard et al. | |
| 4,116,201 A | 9/1978 | Shah | |
| 4,133,303 A | 1/1979 | Patel | |
| 4,140,127 A | 2/1979 | Cianci et al. | |
| 4,212,192 A | 7/1980 | Taylor | |
| 4,219,026 A | 8/1980 | Layton | |
| 4,235,229 A | 11/1980 | Ranford et al. | |
| 4,315,505 A | 2/1982 | Crandall et al. | |
| 4,419,095 A | 12/1983 | Nebergall et al. | |
| 4,471,776 A | 9/1984 | Cox | |
| 4,674,495 A * | 6/1987 | Orr ....................... 128/207.14 |
| 4,710,175 A * | 12/1987 | Cartmell et al. ............. 604/177 |
| 4,713,070 A * | 12/1987 | Mano ........................ 623/1.39 |
| 4,817,598 A | 4/1989 | LaBombard | |
| 4,852,565 A * | 8/1989 | Eisele ................... 128/207.14 |
| 4,924,862 A | 5/1990 | Levinson | |
| 4,987,895 A | 1/1991 | Heimlich | |
| 5,058,580 A | 10/1991 | Hazard | |
| 5,112,312 A * | 5/1992 | Luther ....................... 604/177 |
| 5,217,005 A | 6/1993 | Weinstein | |
| 5,217,007 A | 6/1993 | Ciaglia | |
| 5,230,332 A | 7/1993 | Strickland | |
| 5,460,176 A * | 10/1995 | Frigger .................. 128/207.14 |
| 5,487,383 A | 1/1996 | Levinson | |
| 5,515,844 A | 5/1996 | Christopher | |
| 5,546,936 A * | 8/1996 | Virag et al. ............ 128/207.14 |
| 5,626,132 A | 5/1997 | Miller et al. | |
| 5,669,380 A * | 9/1997 | Garry et al. ............ 128/207.14 |

(Continued)

FOREIGN PATENT DOCUMENTS

DE   197 07 364 C   12/1997

(Continued)

OTHER PUBLICATIONS

Extended European Search Report 08000133.2—2310 / 1923090, 7 pages, mailed Aug. 19, 2008.

*Primary Examiner*—Steven O Douglas (57) ABSTRACT

The preferred embodiments provide, e.g., a high quality flexible tracheostomy tube assembly including an outer tracheostomy cannula and a disposable, flexible inner cannula. In preferred embodiments, the product provides a single patient use, sterile device.

20 Claims, 9 Drawing Sheets

U.S. PATENT DOCUMENTS

| | | | |
|---|---|---|---|
| 5,762,638 A | | 6/1998 | Shikani et al. |
| 5,819,723 A | | 10/1998 | Joseph |
| 6,099,506 A | * | 8/2000 | Macoviak et al. ............ 604/173 |
| 6,105,577 A | * | 8/2000 | Varner ................... 128/207.17 |
| 6,135,110 A | | 10/2000 | Roy |
| 6,135,111 A | | 10/2000 | Mongeon |
| 6,168,212 B1 | * | 1/2001 | Finley ........................ 285/377 |

FOREIGN PATENT DOCUMENTS

| | | |
|---|---|---|
| DE | 19707364 C1 | 12/1997 |
| DE | 102 13 950 A | 10/2002 |
| EP | 0371752 A | 6/1990 |
| EP | 0 872 253 A2 | 10/1998 |
| WO | WO 94/01156 A | 1/1994 |
| WO | WO 95/04566 A1 | 2/1995 |
| WO | WO 97/37702 A1 | 10/1997 |

* cited by examiner

FIG. 1 insert and rotate

FIG. 2

| Product Size | I.D. (mm) | O.D. (mm) | Length (mm) | Leak Test Inflation Volume (cc) | Cuff Resting Diameter (mm) |
|---|---|---|---|---|---|
| 6 | 6.0 | 8.3 | 64 mm | 11 | 19 |
| 7 | 7.0 | 9.6 | 70 mm | 14 | 21 |
| 8 | 8.0 | 10.8 | 74 mm | 20 | 24 |
| 9 | 9.0 | 12.1 | 80 mm | 22 | 27 |
| 10 | 10.0 | 13.3 | 80 mm | 29 | 30 |

FIG. 10

MULTIPLE CANNULA SYSTEMS AND METHODS

BACKGROUND

1. Field of the Invention

The present invention pertains generally to multiple cannula systems and methods and some preferred embodiments pertain to dual cannula tracheostomy tube systems and methods.

2. Description of the Related Art

Cannula assemblies are often used in medical processes. For example, in performing a typical tracheotomy, a surgeon often surgically creates an opening in a patient's neck and into the patient's trachea (i.e., windpipe). In this illustrative context, a cannula is often placed through this opening (i.e., tracheostomy tube or a trach tube) to provide an airway and/or to enable secretions to be removed. Cannulas are also used in a variety of other medical environments.

Illustrative medical systems and processes employing, e.g., cannulas are shown, by way of example, in the following references, the entire disclosures of which are incorporated herein by reference in their entireties: U.S. Pat. No. 6,135,110 entitled Tracheostomy Tube; U.S. Pat. No. 6,105,577 entitled Advanced Tracheostomy Tube And Oral Endotracheal Tube Holder; U.S. Pat. No. 5,819,723 entitled Methods And Apparatus For Reducing Tracheal Infection; U.S. Pat. No. 5,762,638 entitled Anti-Infective And Anti-Inflamatory Releasing Systems For Medical Devices; U.S. Pat. No. 5,626,132 entitled Tracheal Tube With Built-In Vocalization Capability; U.S. Pat. No. 5,515,844 entitled Method And Apparatus For Weaning Ventilator-Dependent Patients; U.S. Pat. No. 5,487,383 entitled Tracheal Tube Cuff Inflation Control And Monitoring System; U.S. Pat. No. 5,230,332 entitled Methods And Apparatus For A Micro-Tracheal Catheter HUB Assembly; U.S. Pat. No. 5,217,007 entitled Speculum For Forming An Ostomy In A Trachea; U.S. Pat. No. 5,217,005 entitled Apparatus For Performing Percutaneous Tracheostomies And Cricothyoidectomies; U.S. Pat. No. 4,987,895 entitled Tracheal Tube; U.S. Pat. No. 4,924,862 entitled Pressure Controller And Leak Detector For Tracheal Tube Cuff; U.S. Pat. No. 4,817,598 entitled Tracheostomy Tube With Ring Pull Removable Inner Cannula; U.S. Pat. No. 4,471,776 entitled Static Tracheostomy Tube; U.S. Pat. No. 4,419,095 entitled Cannula With Radiopaque Tip.; U.S. Pat. No. 4,315,505 entitled Tracheostomy Tube With Disposable Inner Cannula; U.S. Pat. No. 4,235,229 entitled Adjustable Tracheostomy Tube Assembly.

Existing cannula systems had a variety of limitations. The present invention was made in view of these and/or other limitations in the related art.

SUMMARY OF THE PREFERRED EMBODIMENTS

The preferred embodiments of the present invention provide substantial improvements over the above-mentioned and/or other systems and methods in the related art.

According to some embodiments, a multiple cannula assembly for insertion into a patient includes: a flexible outer cannula having a proximal head; a flexible inner cannula having a proximal hub; the inner cannula being longitudinally insertable into the outer cannula to an insertion position with the hub inside the head; the head including at least one ridge and the hub including at least one protrusion, the hub being rotatable to a locked position with the at least one protrusion under the at least one ridge upon rotation of the hub within the head from the insertion position; the head including a connector to connect to respiratory equipment in the locked position. Preferably, the protrusion is locked upon rotation of the hub about ¼ turn clockwise. In some embodiments, the assembly includes an expandable cuff. And, in some embodiments, the outer cannula includes a percutaneous tip. Preferably, the hub includes a knurled portion that extends from the head when in the locked position.

According to other embodiments, a multiple cannula-assembly for insertion into a patient includes: a flexible outer cannula having a proximal head; a flexible inner cannula having a proximal hub; the inner cannula being longitudinally insertable into the outer cannula to an insertion position with the hub proximate the head; the flexible inner cannula being made with PTFE. Preferably, the PTFE includes nodes and fibers. Preferably, the nodes are arranged around a circumference of the inner cannula and/or the fibers are oriented along a length of the cannula.

According to other embodiments, a multiple cannula assembly for insertion into a patient includes: a flexible outer cannula having a proximal head; a flexible inner cannula having a proximal hub; the inner cannula being longitudinally insertable into the outer cannula to an insertion position with the hub proximate the head; the inner cannula being made with a material having fibers oriented along a length of the cannula and nodes around a circumference of the cannula.

According to some embodiments, a multiple cannula assembly for insertion into a patient includes: a flexible outer cannula having a proximal head; a flexible inner cannula having a proximal hub; the inner cannula being longitudinally insertable into the outer cannula to an insertion position with the hub proximate the head; the outer cannula including a substantially rigid tip portion and a substantially flexible portion, the substantially rigid tip portion being made with a rigid PVC material having a shore D hardness of between about 55 to 65 and the substantially flexible portion being made with a flexible PVC material having a shore A hardness of between about 80 to 90. Preferably, the substantially rigid tip includes a substantially conical front-section, a large-diameter substantially cylindrical mid-section, a downward step, and a small-diameter substantially cylindrical rear-section. In some embodiments, the rigid PVC material has a shore A hardness of more than 15 greater than the shore A hardness of the substantially flexible portion, or, preferably, more than 20 greater than the shore A hardness of the substantially flexible portion.

The above and/or other aspects, features and/or advantages of various embodiments will be further appreciated in view of the following description in conjunction with the accompanying figures. Various embodiments can include and/or exclude different aspects, features and/or advantages where applicable. In addition, various embodiments can combine one or more aspect or feature of other embodiments where applicable. The descriptions of aspects, features and/or advantages of particular embodiments should not be construed as limiting other embodiments or the claims.

BRIEF DESCRIPTION OF THE DRAWINGS

The accompanying figures are provided by way of example, without limiting the broad scope of the invention or various other embodiments, wherein.

DETAILED DESCRIPTION OF THE PREFERRED EMBODIMENTS

In some preferred embodiments, a multiple cannula system is provided that includes an outer cannula and a substantially co-axial inner cannula. Preferably, the outer cannula is an arcuate shaped flexible tube with a disposable inner cannula. In the most preferred embodiments, the multiple cannula system is a tracheostomy tube system. However, various embodiments and/or aspects of various embodiments can involve multiple cannula assemblies for other purposes and/or environments.

In some embodiments, the system can include a percutaneous tracheostomy tube structure. In addition, in some embodiments, the system can include an expandable (e.g., inflatable) cuff. In some examples, cuffed products can be used with percutaneous dilatational tracheotomy (PDT) procedures. In various embodiments, the assembly can incorporate features (such as, e.g., materials, etc.) of existing cannula tube systems and methods, such as, e.g., that set forth in the above-noted patents incorporated herein by reference.

Preferably, the device can be placed in a patient surgically and/or percutaneously in, e.g., an acute care setting. In some embodiments, the tracheostomy tubes are generally temporary and provide a method for ventilation that can be, e.g., more comfortable and less problematic than long-term endotracheal intubation. The tracheostomy tubes can preferably provide an artificial airway that will improve airway access for clearing secretions, permitting voice restoration and/or improving pulmonary status by reducing the work of breathing and/or lowering physiological dead-space. In various embodiments, the device can be used to provide an artificial airway in order to assist in the treatment of a variety of respiratory diseases and/or in airway management for patients.

In some embodiments, the devices can be implemented by ear-nose-throat specialist physicians (ENTs) and/or any other physicians performing surgical and/or percutaneous tracheostomy procedures. The product can be used, e.g., with critically ill and/or injured patients that require, e.g., substantially long-term security of their airway and/or substantially long-term ventilation.

In some embodiments, a variety of tracheostomy tube systems can be provided having different sizes. For example, sizes can range, in some embodiments, between about sizes of 6, 7, 8, 9 and 10 mm for the inside diameter (I.D.) of an outer cannula (not including, e.g., cuff features). In some embodiments, a tracheostomy tube system can include one or more of the following features:

- a flexible outer cannula with a flexible disposable inner cannula;
- the outer cannula can be cuffed or uncuffed;
- the outer cannula can include a percutaneous tip (which can be made, e.g., compatible with a percutaneous dilatational loading dilator) or a dilatational tracheostomy (PDT) style tip; and/or
- a cuff pressure indicator (CPI)(in some embodiments, the assembly can employ, by way of example, one or more of the indicator devices shown in U.S. Pat. Nos. 4,074,714, 4,116,201 or 4,133,303 of The Kendall Company).

Preferably, the system is based on a modular product platform. For example, the product design can be modular in nature. A modular design platform can allow, e.g., the manufacture of many different but specific end design product configurations. In preferred embodiments, the inner and outer cannulas are bendable and flexible.

In some embodiments, the product can be packaged as follows: individual assemblies can be packaged in, e.g., trays, while a plurality of trays can be packaged together as a unit in a carton. Preferably, disposable inner cannulas are packaged in trays, while, for example, about ten such trays can be packaged in a carton. In preferred embodiments, additional disposable inner cannulas can be purchased separately.

In some embodiments, the product is provided to the customer in a sterile condition (e.g., in a sterile package). In some examples, the method of sterilization can include ethylene oxide (EtO) gas sterilization. In some embodiments, the device is used for only a single patient and/or a single use.

In preferred embodiments, the materials used will perform appropriately after exposure to at least some, preferably all, of the following chemical/cleaning agents: isotonic saline solution; water soluble lubricants or gels; typical disinfectant solutions; isopropyl alcohol and water. In preferred embodiments, the materials used will perform appropriately after repeated exposure to common respiratory drug aerosols including: bronchodilators; steroids; mucolytics; surfactants; antibiotics; and/or their related gas and/or liquid propellants (perflourocarbons [CFCs and CFC-free PFCS], methanes, alcohols, etc.). In preferred embodiments, the materials used shall perform appropriately during and after exposure to conventional anesthetic gases in clinically expected concentrations including, e.g.: flourane and/or halothane. In preferred embodiments, the materials used shall pass ISO 10993-1 biological safety tests appropriate for their intended use. In preferred embodiments, the materials used and the packaging shall be Latex free.

Figure 1:
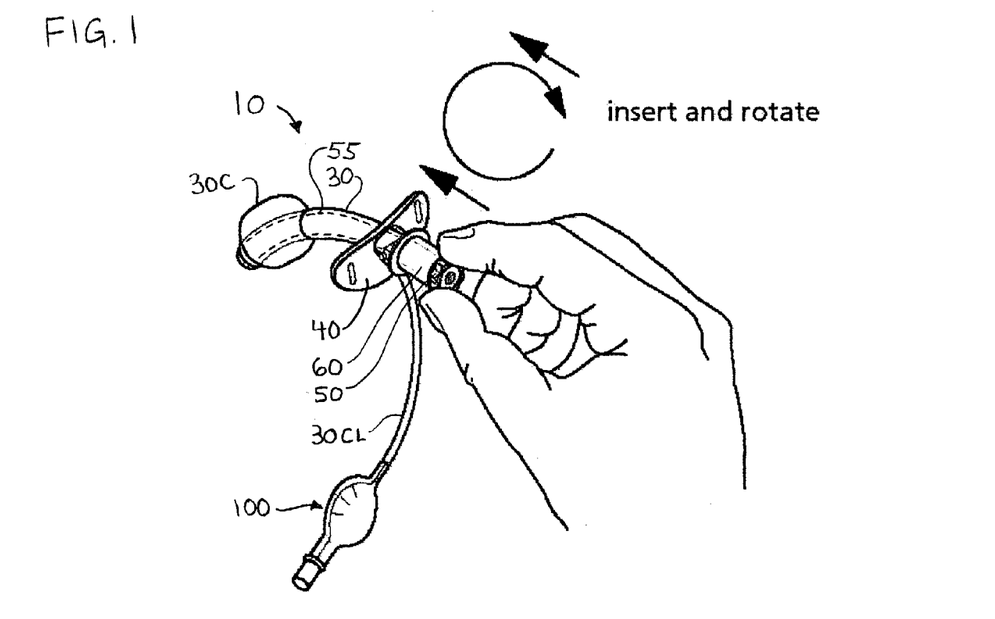
FIG. 1 is a perspective view of an assembly according to some illustrative embodiments of the invention being manipulated via a user's hand.

FIGS. 1-9 show some illustrative embodiments of the invention. In this regard, FIG. 1 shows a tracheostomy tube assembly including, an outer cannula 30 having a head 60 fixed at a proximal end, an inner cannula 55 (shown in dashed lines) having a hub 50 fixed at a proximal end (the hub 50 shown protruding slightly from the head 60); a neck flange 40; an inflatable cuff 30C; and a pilot balloon 100 for inflating the inflatable cuff. While a wide variety of embodiments are encompassed by this disclosure, in some illustrative embodiments, the parts can be made substantially in proportion to that shown in the figures. For example, in some embodiments, the parts can be made substantially as shown in one or more of the FIGS. 1-9, with such figures being proportional and to scale as shown in various illustrative and non-limiting embodiments of the invention.

Figure 2:
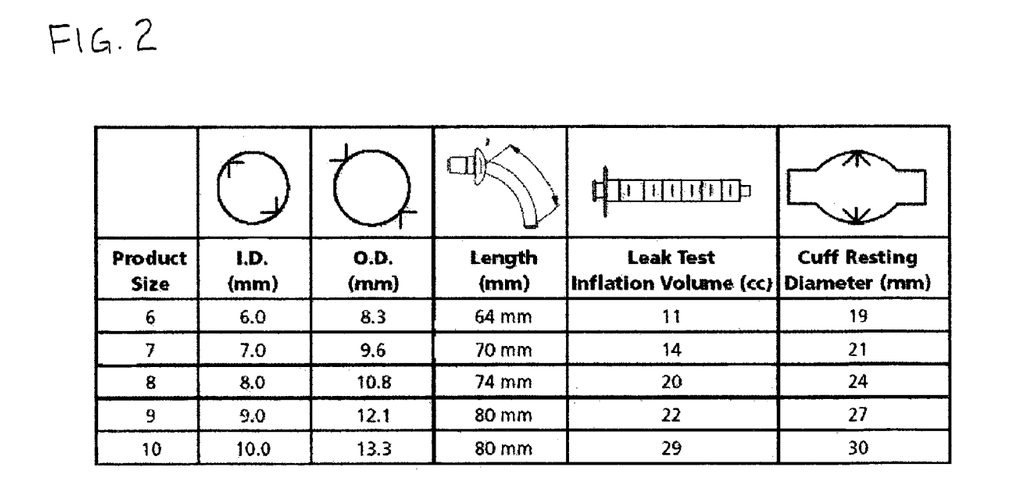
FIG. 2 is a table depicting some illustrative features according to some illustrative and non-limiting embodiments of the invention.

FIG. 2 is a table depicting some illustrative and non-limiting examples of dimensions for an outer cannula in some illustrative embodiments of the invention, including product sizes 6-10, having respective inside diameter (I.D.) in millimeters, outside diameter (O.D.) in millimeters, and lengths in millimeters. FIG. 2 also depicts some illustrative dimensions of the cuff in a resting condition along with inflation volumes in the illustrative embodiments shown. It should be understood that these illustrative embodiments are merely illustrative and do not limit the wide range of the various embodiments that may be constructed.

Outer Cannula

In some preferred embodiments, the outer cannula is a generally flexible tube. Preferably, the outer cannula has a generally constant cross-sectional shape. The outer cannula can be constructed of a variety of materials. In some preferred embodiments, it can be constructed with, for example, a flexible polyvinyl chloride (PVC). In some embodiments, the outer cannula can be manufactured in a variety of sizes, such as, by way of example only, 6.0, 7.0, 8.0, 9.0 and 10.0 mm internal diameter sizes as shown in FIG. 2. In some embodiments, the outer cannula can be substantially clear with, e.g., a radio opaque portion(s) or line(s). Preferably, the outer cannula 30 is made with biocompatible materials. In some embodiments, the cannula 30 can be made with a material having a Shore A Hardness of about between about 70 to 100, or, more preferably, between about 75 to 95, or, more preferably, between about 80 to 90, or, more preferably, between about 82 to 88, or, more preferably, about 85. In some preferred embodiments, the outer cannula 30 has a Shore A Hardness of 85 plus-or-minus 3.

In the most preferred embodiments, the outer cannula 30 is formed by extrusion. For example, the outer cannula can preferably be formed by the forcing of softened polymeric material through the orifice of a die to produce a continuous product of a controlled cross section, using an extruder.

Figure 3A:
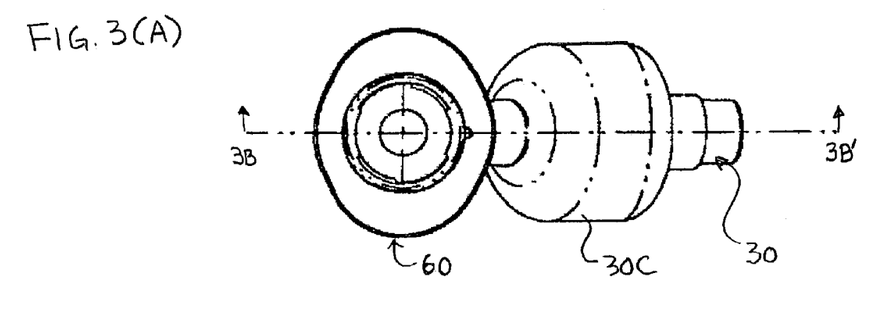
FIG. 3(A) is a top view of an assembly including an outer cannula having an attached head and an inflatable cuff according to some illustrative embodiments of the invention.
Figures 3B, 3C:
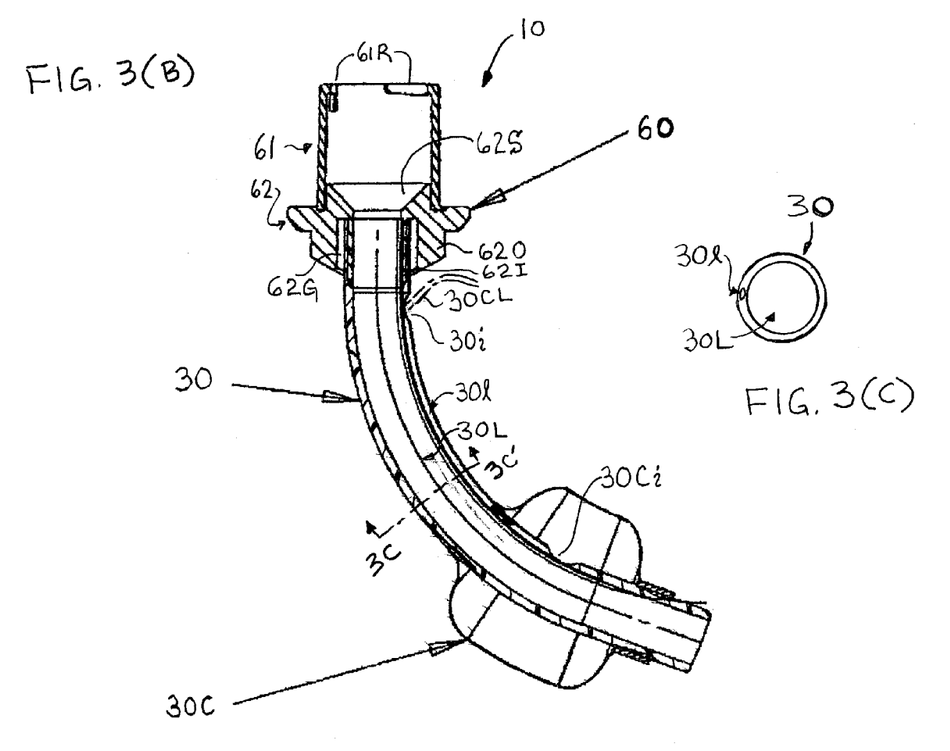
FIG. 3(B) is a cross-sectional view of the assembly shown in FIG. 3(A) taken along the line 3B-3B' shown in FIG. 3(A)
FIG. 3(C) is a cross-sectional view of the assembly shown in FIG. 3(A) taken along the line 3C-3C' shown in FIG. 3(B).

As shown in FIGS. 3(B) and 3(C), the cannula 30 preferably includes a large substantially circular internal lumen 30L that, among other things, receives the inner cannula 55 (as described below) and a small airway lumen 30*l* that extends inside a length of the wall of the cannula 30 between an air inlet 30*i* and a cuff inlet 30Ci to supply/return air to/from the cuff 30C. Preferably, the lumen 30*l* does not communicate with the lumen 30L (e.g., such that air within the lumen 30*l* will not enter the lumen 30L). As shown in dashed lines in FIG. 3(B), the line 30CL can be connected to the inlet 30*i* to supply air therein. In some embodiments, the lumen 30*l* can be formed during extrusion and, then, after extrusion inlets 30*i* and 30Ci can be formed (e.g., by cutting) and the lumen 30*l* can be sealed at proximal and distal ends to provide a sealed air passage. In some embodiments, the lumen 30*l* can be formed after extrusion of the cannula. Of course, while extrusion is preferred, the cannula can be formed using numerous other methods (such as, e.g., various molding methods).

In some embodiments, as shown in FIGS. 3(A) and 3(B), the outer cannula has a head 60 fixed thereto. Preferably, the head includes a connector portion 61 and a base portion 62. In some illustrative embodiments, the connector 61 can be a 15 mm connector (e.g., the diameter D, shown in FIG. 6(C), can be, e.g., about 15 mm or about 0.599 inches in some illustrative embodiments). Preferably, the head 60 is bonded securely to the outer cannula 30 via the base portion 62 and does not detach under normal use conditions. In some embodiments, the base portion 62 and the connector portion 61 can be integrally formed together (e.g., as a single, integrally molded piece). In some embodiments, the base portion 62 and the connector portion 61 can be welded and/or otherwise connected together (such as, e.g., via ultrasonic welding). In some embodiments, the head 60 can be molded to and/or integrally formed with the outer cannula 30. Preferably, the base 62 of the head includes two locking detentions or holes 62H, shown in FIG. 6(A)), for receiving arms 40F extending from the flange 40 so as to retain the flange 40 in a pivoting and/or swiveling manner on the head base. Preferably, the head base also includes a seat 62S for a hub of the inner cannula. In some embodiments, the head (including the base 62 and/or the connector 61) can be formed with, e.g., acrylonitrile butadiene styrene (ABS). In some embodiments, the head can be colored, such as, e.g., white.

As shown in FIG. 3(B), the base 62 preferably includes a seat 62S (such as, e.g., including a conical surface as shown), an outer depending cylindrical extension 62O, an inner depending cylindrical extension 62I, and a cylindrical recess or groove 62R between the outer and inner extensions 62O and 62I. As shown in FIG. 3(B), a proximal end of the outer cannula 30 can be received in the cylindrical recess 62R for attachment thereto. Preferably, in embodiments having an inner extension 62I, the extension 62I has a thin cross-sectional width so as to minimize interference during insertion of an inner cannula and to maximize the size of the inner cannula that can be inserted. For example, in some illustrative and non-limiting embodiments that can be used with products listed in FIG. 2, the width of the extension 62I is preferably less than about 0.03 inches, or, preferably, about 0.027 inches or less.

Different Flexibilities

In some embodiments, the outer cannula 30 can include portions with substantially different flexibilities (such as, e.g., substantially different durometer characteristics). In general, it can be desirable to have a trach tube that is flexible so as to enable it to bend and curve to different physiologies such that it can be inserted into a wide variety of patients relatively easily. However, in some instances, when the end of the outer cannula is very flexible, insertion into the airway can be somewhat difficult.

In some embodiments, the outer cannula is formed with an end portion that includes a material that is substantially stiff (e.g., substantially rigid). As shown, for example, in FIGS. 7-8, an outer cannula can include an end portion 70 that is made with a substantially stiff material and which is attached to a portion 30' that is made of a substantially flexible material at a junction 71. For example, the cannula portion 30' can be made with materials like that used for the cannula 30 described in various embodiments herein. In some embodiments, the materials can be bonded together using an RF welding process. For example, in some embodiments, the materials can be bonded together using one or more materials and/or processes described in U.S. Pat. No. 4,419,095, the entire disclosure of which is incorporated herein by reference. In some embodiments, the materials are bonded together by continuous extrusion of two different and mutually chemically compatible elements. For example, in some embodiments, the materials can be bonded together using one or more materials and/or processes described in PCT International Publication No. WO 97/37702, published Oct. 16, 1997, entitled Bronchoaspiration Tube Having Soft And Hard Portions, the entire disclosure of which is incorporated herein by reference. In illustrative embodiments employing an extrusion, the tip and cannula 30' portions would be made with substantially continuous cross-sections, but could be, e.g., modified after extrusion (if desired).

Figure 7:
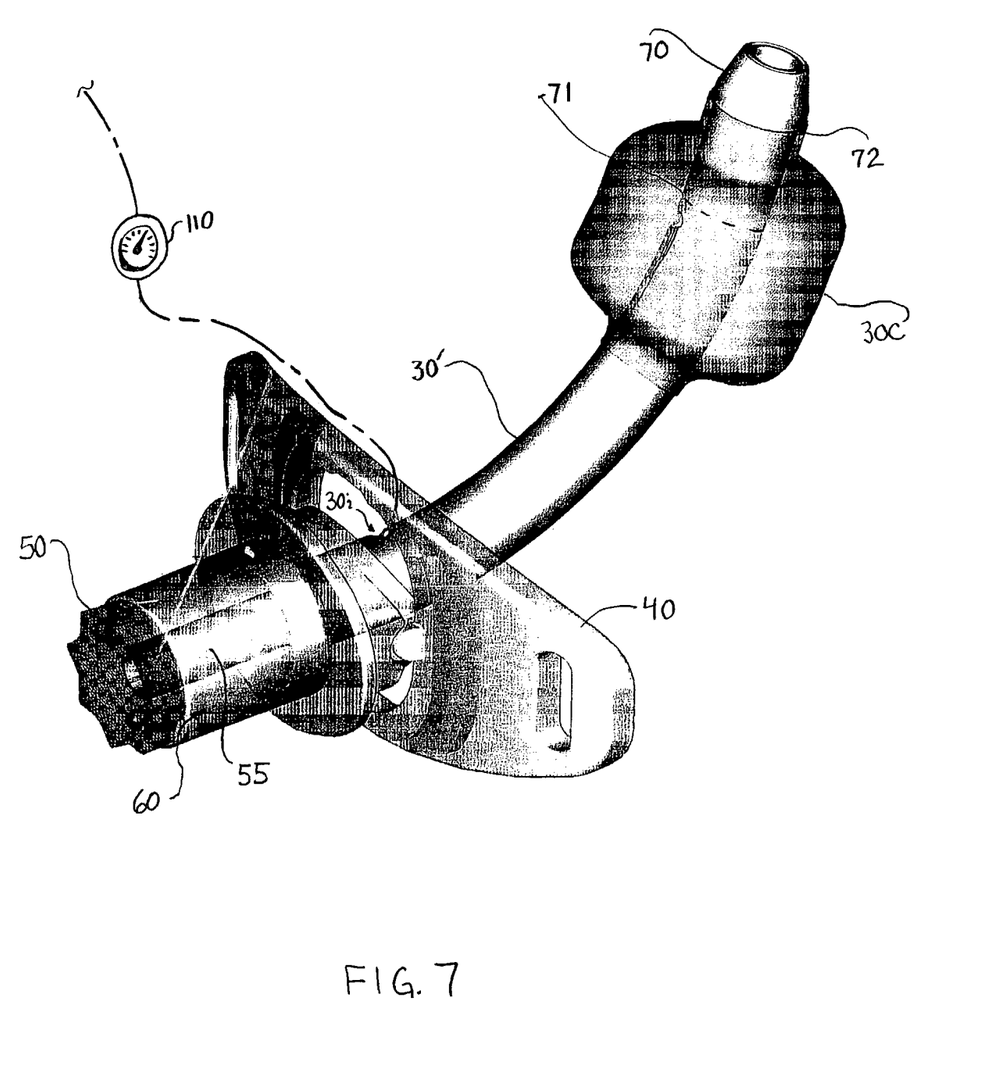
FIG. 7 is a perspective view of a multiple cannula assembly according to some illustrative embodiments of the invention including a stiffened tip portion.
Figure 8:
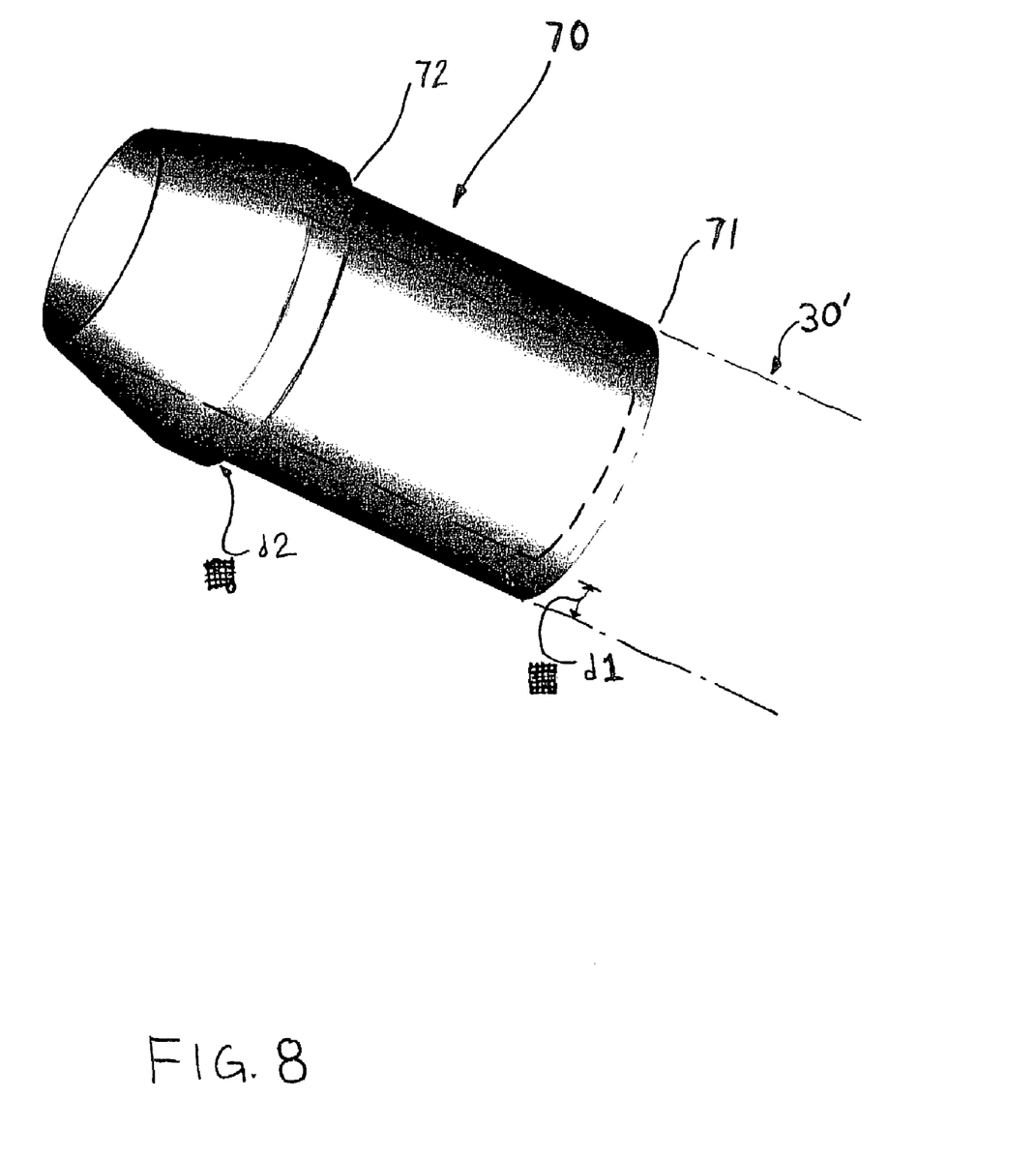
FIG. 8 is a perspective view showing an outer cannula including a stiffened tip portion as shown in FIG. 7.

In some embodiments, the tip portion 70 has a Shore D hardness of about 50 to 70, or, more preferably, about 55 to 65, or, more preferably, about 60. In some illustrative embodiments, the tip portion 70 has a Shore D hardness of about 60 plus-or-minus 2. In some illustrative embodiments, the tip portion 70 can have a Shore A hardness of about 105 to 115. In some embodiments, the tip portion 70 can be made with a rigid PVC.

In some embodiments, the cannula portion 30' can be made with a material having a Shore A Hardness of about between about 70 to 100, or, more preferably, between about 75 to 95, or, more preferably, between about 80 to 90, or, more preferably, between about 82 to 88, or, more preferably, about 85. In some preferred embodiments, the outer cannula portion 30' can have a Shore A Hardness of 85 plus-or-minus 3.

In some embodiments, the tip 70 can have a total length of between about 0.4 to 0.8 inches, or, preferably, about 0.6 inches. In some embodiments, the tip can have a wall cross-sectional width d1 that is about equal to the cross-sectional width of the cannula 30' such as, e.g., comparable to the embodiments shown in FIG. 2 in some illustrative cases (e.g., wherein O.D. minus I.D. multiplied by ½ equals the cross-sectional wall width).

In tests of some preferred embodiments, strengths of parts of the device according to some embodiments have been found to withstand separation forces of well over 11 lbs, such as, e.g., well over about 20 lbs, and even over about 40 lbs, and even over about 60 lbs of force in some embodiments. Here, separate forces include longitudinal forces applied between the tip 70 and the portion 30'.

Stepped Portion

In some embodiments, the outer cannula includes a downward step portion 72 as shown, by way of example, in FIGS. 7-8. Although FIGS. 7-8 depict embodiments with a stiffer tip 70, a stepped portion 72 could also be applied in embodiments which do not include such a stiffer tip 70.

Among other things, the stepped portion can most advantageously be used in conjunction with embodiments including a cuff. In this regard, when the cuff is formed around the outer cannula, an outwardly bulge or shoulder created by the cuff can be substantially or entirely eliminated. In this manner, the device can, e.g., be more easily surgically or percutaneously inserted into a patient with a very low force/insertion force. In some embodiments, the stepped portion 72 extends inward about 0.01 to 0.02 inches, or, more preferably, about 0.013 to 0.017 inches, or, preferably, about 0.015 inches.

Inner Cannula

Figure 5A:
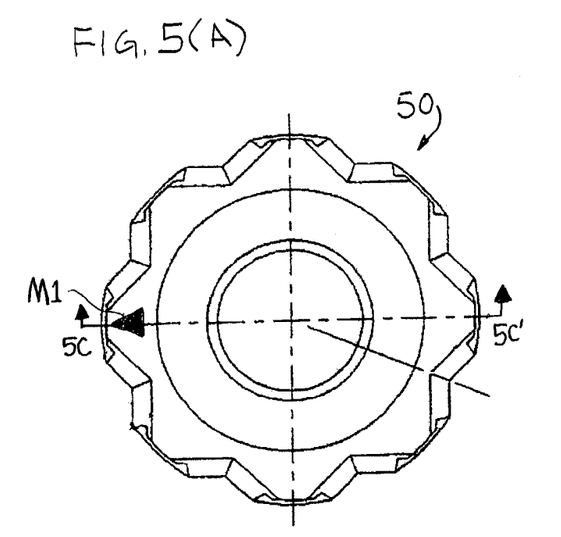
FIG. 5(A) is an end view of a hub that can be attached to an inner cannula in some illustrative embodiments.
Figure 5B:
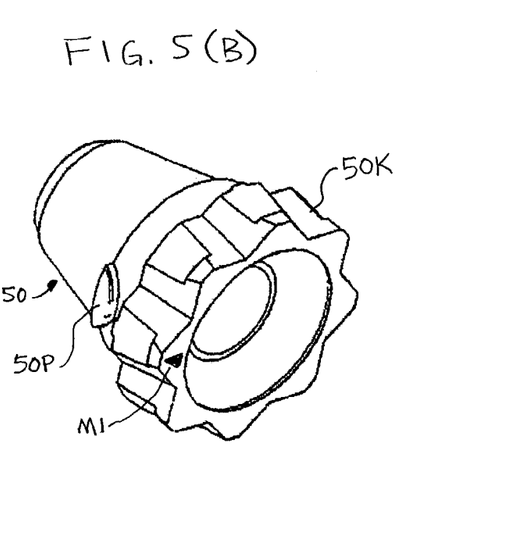
FIG. 5(B) is a perspective view of the hub shown in FIG. 5(A)
Figure 5C:
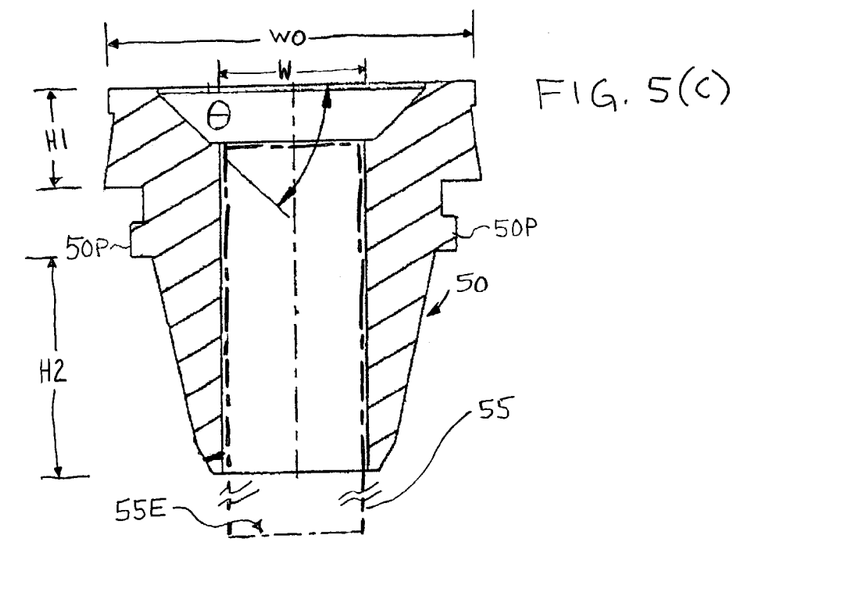
FIG. 5(C) is a cross-sectional view of the hub shown in FIG. 5(A), attached to an inner cannula, and taken along the line 5C-5C' shown in FIG. 5(A).
Figure 6A:
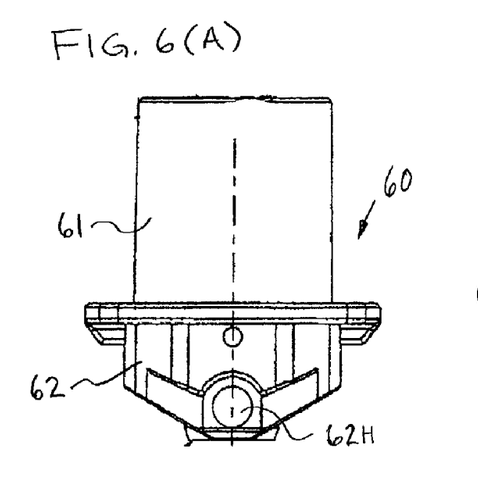
FIG. 6(A) is a front view of a head that can be attached to an outer cannula in some illustrative embodiments.
Figure 6B:
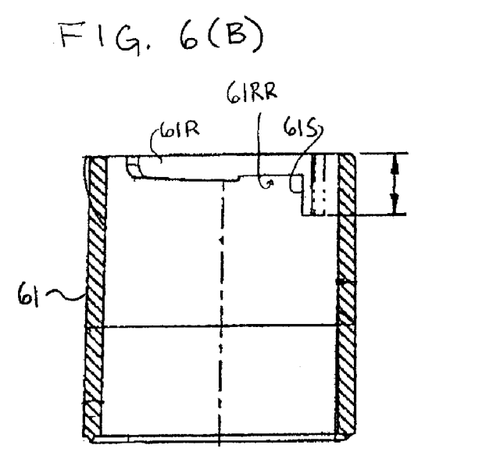
FIG. 6(B) is a cross-sectional side view of a connector portion of the head shown in FIG. 6(A) taken along the line 6B-6B' shown in FIG. 6(D)
Figure 6C:
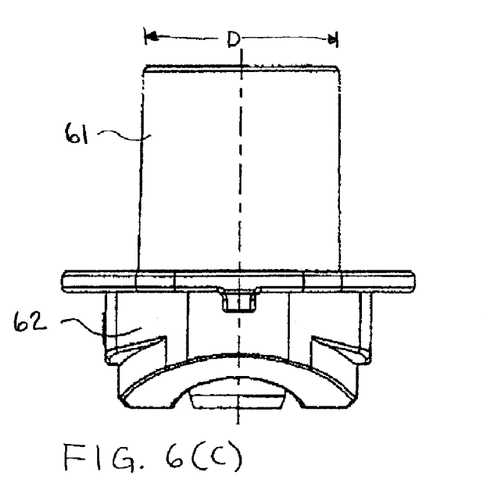
FIG. 6(C) is a side view of the head shown in FIG. 6(A) from substantially perpendicular to the view shown in FIG. 6(A)
Figure 6D:
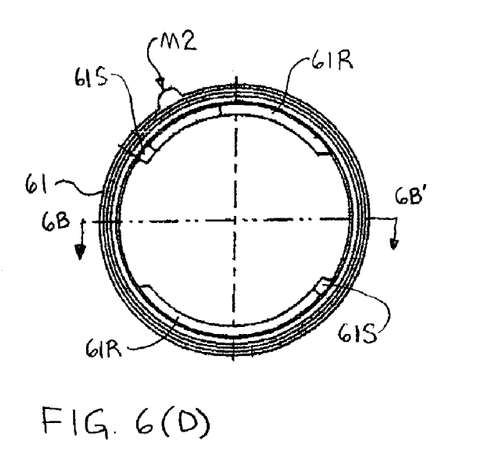
FIG. 6(D) is a top view of the connector portion of the head shown in FIG. 6(A) looking downward into the head in FIG. 6(A).

In some embodiments, a flexible inner cannula 55 is included. Preferably, the inner cannula 55 is disposable and/or replaceable. In that regard, the inner cannula is preferably designed to be easily removed from the outer cannula 30. Preferably, the inner cannula 55 is sufficiently flexible to accommodate the shape of the outer cannula into which it is placed with a low insertion force and/or with a low removal force. The inner cannula preferably does not kink during use. In addition, the inner cannula 55 preferably has a length that substantially matches the length of the outer cannula at its distal tip (i.e., the end of the inner cannula 55E, see FIG. 5(C), is preferably commensurate with the end of the outer cannula). In some embodiments, alignment members and/or marks M1, M2, such as shown in, e.g., FIG. 5(A) and 6(D), can be provided on the inner and outer cannula connectors to help depict when they are locked (see below regarding connection process steps).

In the most preferred embodiments, the inner cannula 55 is also formed by extrusion. Once again, such extrusion can include, e.g., the forcing of softened polymeric material through the orifice of a die to produce a continuous product of a controlled cross section, using an extruder. Of course, while extrusion is preferred, the cannula can be formed using numerous other methods (such as, e.g., various molding methods).

In some preferred embodiments, the inner cannula includes a hub 50 fixed to its proximal end. In some embodiments, the hub includes a twist-lock connector that secures inside a respective connector in the outer cannula (such as, e.g., within a 15 mm connector on the tracheostomy tube). Preferably, the hub 50 includes a ridged or knurled portion 50K so as to facilitate manual operation (e.g., rotation) of the hub 50 such as shown in FIG. 1. In addition, the hub 50 preferably includes a plurality of protrusions 50P that are configured to lock under the locking members 61R on the head shown in FIGS. 3(B), 6(B) and 6(D) when inserted past the locking members and rotated to a position under the locking members. Preferably, the protrusions 50P have a rounded top surface to facilitate entry under the members 61R during this rotation. In preferred embodiments, the protrusions 50P can slide under the members 61R into a recess 61RR of the head adjacent an end stop 61S that abuts the protrusions 50P to prevent further rotation.

In some preferred embodiments, the tube 55 can be formed with a polytetrafluoroethylene (PTFE) material. The tube can, in some embodiments, be colored, such as, e.g., white. In some embodiments, the hub can be made with a variety of appropriate materials, such as, e.g., polymer materials that are substantially rigid. In some illustrative embodiments, the hub can have a color, such as, e.g., white. In some preferred embodiments, the hub can be bonded to the inner cannula using an overmolding process. Preferably, the hub is adapted to lock the inner cannula within the outer cannula.

In some embodiments, the inner cannula is made with a high density porous expanded PTFE (ePTFE). For example, in some embodiments, the density can be about 1.2+0.0−0.1 g/ccm. In other illustrative embodiments, the density can vary from the above by about, for example, plus-or-minus 5%, or, in other embodiments, about plus-or-minus 10%, or, in other embodiments, about plus-or-minus 25%, or, in other embodiments even more.

In some embodiments, the inner cannula has a substantially constant cross-sectional shape as is substantially cylindrical with open ends on distal and proximal ends. In some embodiments, the ends of the cylindrical cannula are approximately at about an 85 to 95 degree angle, preferably about a 90 degree angle, to the length of the inner cannula (e.g., when the cannula, which is preferably flexible, is arranged such that its length is along a substantially straight line).

In some illustrative embodiments, the inner cannula can have a wall thickness of between about 0.01-0.02 inches, or, more preferably, between about 0.014-0.018 inches, or, more preferably, between about 0.0145-0.0175 inches, or, more preferably, about 0.016 inches. In some illustrative and non-limiting embodiments, respective inner cannulas usable with the illustrative outer cannula product sizes 6, 7, 8, 9 and 10 in FIG. 2 can have inner diameters of, e.g., about 0.186, 0.226, 0.265, 0.298, and 0.338 inches, respectively. In some illustrative and non-limiting embodiments, respective inner cannulas usable with the illustrative outer cannula product sizes 6, 7, 8, 9 and 10 in FIG. 2 can have outer diameters of, e.g., about 0.218, 0.258, 0.297, 0.336, and 0.376 inches (plus-or-minus about 0.005 inches), respectively. Similarly, in some illustrative and non-limiting embodiments, respective hubs 50 usable with the product sizes 6, 7, 8, 9 and 10 in FIG. 2 can have, by way of example: dimensions W of about 0.226, 0.265, 0.304, 0.344, 0.384 inches, respectively; dimensions WO of about 0.5-0.65 inches, or, more preferably, about 0.58 inches; dimensions H1 of about 0.15 inches; dimensions H2 of about 0.35 inches, respectively; and, an angle Θ of about 45 degrees. In some illustrative embodiments, the hub 50 can have dimensions substantially as shown in FIG. 5(A), 5(B) or 5(C), with such figures being shown to scale in some illustrative and non-limiting embodiments.

In some embodiments, the inner cannula can be opaque. In some preferred embodiments, the inner cannula can be configured to lock into a 15 mm connector on an outer tracheostomy cannula. In this manner, the 15 mm connector can be readily adapted for use with standard respiratory equipment.

In some preferred embodiments, TEFLON is used for the inner cannula. The TEFLON inner cannula can be used, in some embodiments, to improve the I.D./O.D. ratio of the tracheostomy tube. Among other things, TEFLON can be advantageous since it can slide in and out of the outer cannula relatively well which can allow the inner cannula outside diameter to be as large as possible which allowing for maximum movement of air. This improved I.D./O.D. ratio can be used to improve airflow through the tube when the inner cannula is in place. The improved airflow can provide lower airway resistance and reduced work required during breathing. In addition, reducing airway resistance can also enhance a weaning process with an improvement in patient acuity and a reduction in the length of stay (LOS) in acute care.

In addition, TEFLON can be used to reduce the propensity of viscous secretions adhering to an inner wall of the inner cannula. A reduction in secretion adherence can, among other things, help to diminish I.D. reduction due to secretions (e.g., clogging). In this regard, when the airway is properly humidified and the patient is properly hydrated, patient secretions can have a lower affinity for adherence to the TEFLON inner cannula.

In the more preferred embodiments, the material of the inner cannula is made with a porous polytetrafluoroethylene (PTFE). In some embodiments, the material can be made using at least some, preferably all, of the following steps:

Granulating: the material preferably begins as a granulated powder.

Mixing: the powder is preferably mixed with, e.g., an ultra-pure mineral spirit that serves as a lubricant during extrusion.

Compressing: the mixture is preferably compressed into a charge.

Loading: the charge is preferably loaded into an extruder (in some preferred embodiments, the extruder is a horizontal extruder design).

Extruding: concentricity is preferably achieved by carefully lining up the tooling of the extruder. A die and a mandrel can be attached. The extrudate can be collected.

Evaporating: plugs can be attached to the ends and the mineral spirits can be evaporated off.

Stretching & Sintering: the material is then preferably stretched in an oven. Then, the material is preferably heated above its melting point (e.g., sintered). The material properties can be solidified during the sintering phase of the process.

Annealing: the airway tube is preferably then subjected to an annealing process.

The annealing process can, e.g., ensure that the material remains round after processing.

Figure 10:
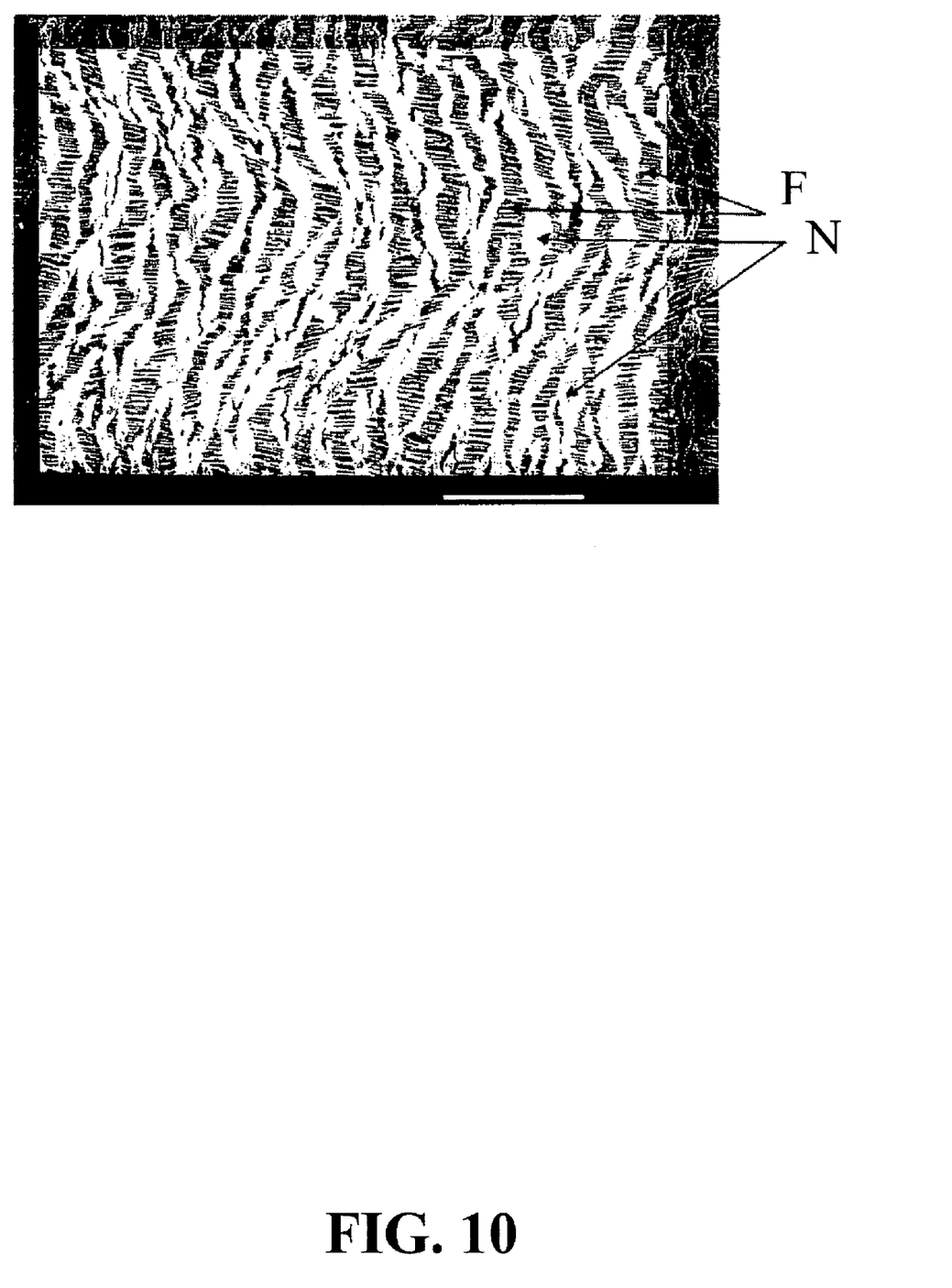
FIG. 10 is a magnified cross-sectional photograph depicting the material of the inner cannula according to some illustrative embodiments of the invention.

In preferred embodiments, the process creates a unique structure of nodes N and fibers F, such as depicted in the magnified photograph shown in FIG. 10. Preferably, the nodes are arranged around the circumference of the tubing and the fibers are oriented along the length of the tubing. In preferred embodiments, this structure allows the material to compress and flex without a significant change in the outer diameter and/or the cross-sectional area. In some embodiments, this can occur because the fibers collapse between the nodes. In this manner, structural integrity of the tubing can be achieved through, e.g., such an arrangement of nodes and fibers, with the nodes providing support around the wall of the tubing making it difficult to collapse.

Among other things, the node and fiber structure facilitates connection of the hub 50 to the inner cannula 55. In this regard, an overmold process is preferably used. While achieving a connection to a TEFLON material could otherwise be difficult because it can be difficult to form a strong hold to the TEFLON, the node and fiber structure enhances the ability of the hub to connect to the cannula 55—such as, e.g., by providing a surface to which the hub can connect and bond to.

In preferred embodiments, the inner cannula is constructed such that when the cannula is bent (such as, e.g., during use), the inner cannula does not fold, block and/or restrict the airway there-through. Among other things, the preferred materials of the inner cannula described herein can advantageously substantially maintain the diameter and/or the cross-sectional area of the inner cannula even during bending. For example, the cross-sectional area of the inner cannula can be maintained substantially constant even when bent within an angle and arc similar to that shown, e.g., in FIG. 3(B) (for example, the angle can be, e.g., about 95, 100, 105 or 110 degrees in some embodiments and the arc can have a radius of curvature of about 1.5 to 2 inches in some embodiments, or, as some examples, about 1.664, 1.765, 1.793 or 1.821 inches).

Neck Flange

Figure 4:
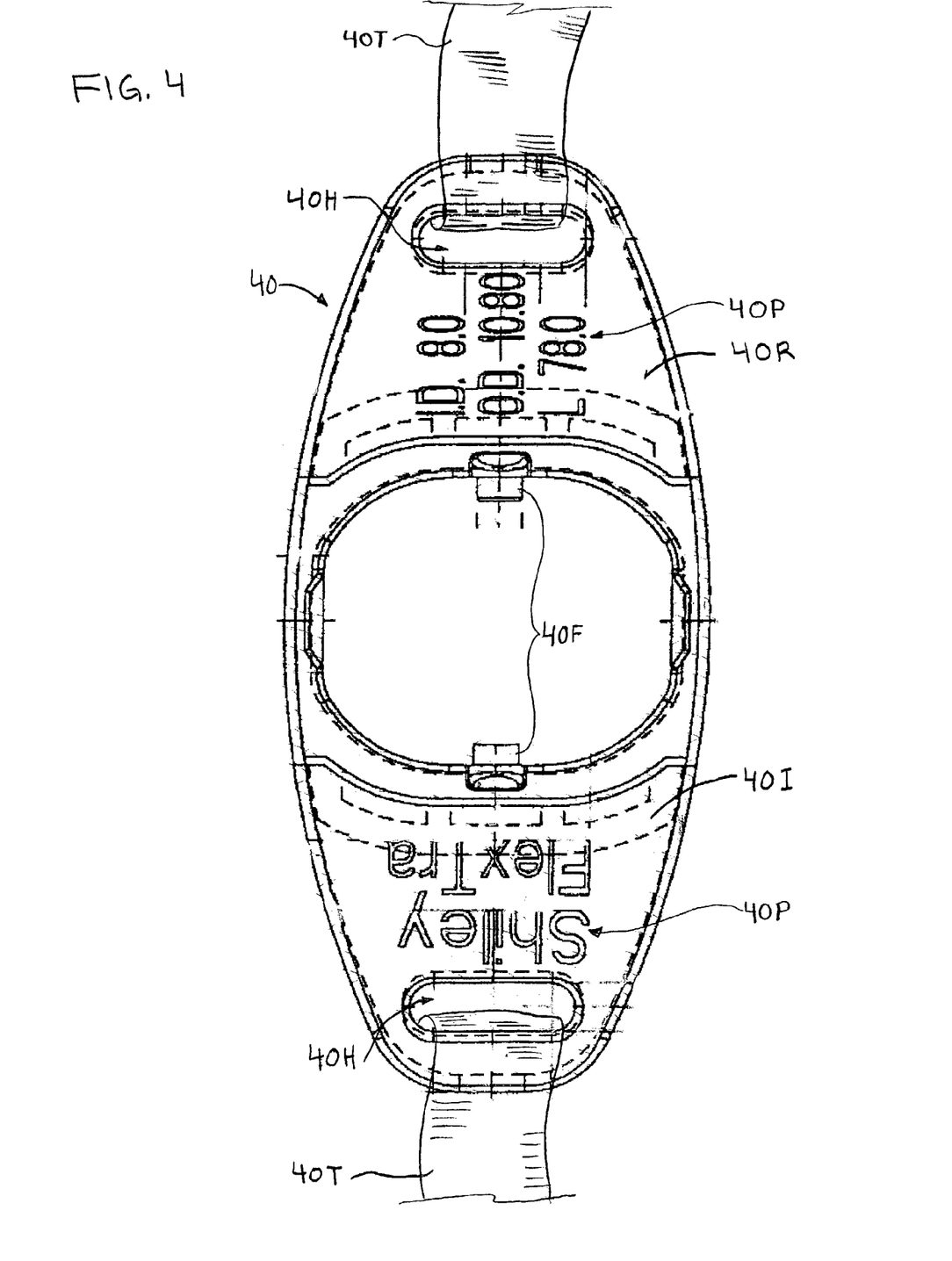
FIG. 4 is a plan view of a neck strap according to some illustrative embodiments of the invention.

In some embodiments, the device includes a pivotally or swivelly mounted neck flange 40, best shown in FIGS. 1 and 4, that provides conformity to fit onto individual neck anatomies. In some embodiments, the neck flange 40 can be provided with tie strap holes 40H for attachment to a tie strap 40T. The tie strap can be, e.g., configured to strap around the patient's neck and may include means to adjust the length, to separate via a buckle and/or clip and/or the like. Preferably, the neck flange 40 is configured to pivot or swivel relative to the outer cannula 30. The range of pivoting or swiveling can be selected depending on circumstances. Preferably, the neck flange is flexible such that it can conform to the contour of an individual patient's neck during use. In preferred embodiments, the neck flange remains in a substantially fixed condition relative to a length of the outer cannula (e.g., in preferred embodiments, it is not longitudinally adjusted along the length of the cannula). Preferably, the neck flange 40 has sufficient integrity to prevent material failure during bending, flexing and/or stress under proper and intended use conditions.

In some embodiments, the neck flange includes an inner ring 40I (shown in dashed lines in FIG. 4) and an outer ring 40R. In some embodiments, the inner ring 40I can be made with a clear polycarbonate material, and the outer flange 40R can be made with a clear PVC material. In some preferred embodiments, the neck flange 40 includes printing 40P thereon related to the product, such as, e.g., product name, I.D., O.D., length and/or style information and/or other information. When such an inner ring 40I is used, the outer ring is preferably fixed thereto, such as using an overmold process. In various embodiments, the neck flange does not include inner and outer rings, but is formed as a single unitarily molded member 40.

Cuff

In some embodiments, the outer cannula includes a cuff 30C. A cuff can be provided, when desired, on models that include a percutaneous tip and/or on models without a percutaneous tip. The cuff is preferably a thin-wall, high-volume and/or low-pressure cuff to minimize tracheal pressure. Preferably, when inflated, the cuff conforms to the natural shape of the trachea providing a seal at low intracuff pressure. In some embodiments, the cuff can be made of a transparent material. In some illustrative embodiments, it can be made with a plastisol material. In some illustrative and non-limiting embodiments, the cuff can include properties as shown in the illustrative table of FIG. 2.

In some embodiments, a cuff inflation line 30CL, such as, e.g., that shown in FIG. 1, preferably includes a luer valve with an integral pilot balloon 100 to effect cuff inflation. In some embodiments, a cuff pressure indicator (CPI), such as, e.g., CPI 110 shown in FIG. 7, is provided to indicate to a clinician when the cuff is inflated to a sufficient pressure after the trach tube is inserted. In some preferred embodiments, the pressure indicator provides a visual display such as, e.g., a digital display, a mechanical display (e.g., a needle, dial, etc.) and/or another display. For example, the cuff pressure indicator can include, e.g., a valve, a pilot balloon, connector tubing (e.g., made with PVC or the like). In some embodiments the cuff pressure indicator can have an operating pressure of about 15-25 cm of $H_2O$.

In some embodiments, during use, to ease insertion during surgical tracheotomy and to guard against cuff perforation from sharp edges of, for example, cartilage, the cuff can be tapered back. For example, this can be accomplished by first inflating the cuff and moving the cuff away from the distal tip of the outer cannula towards the swivel neck plate while the residual air is removed by deflation.

Disposable Cap

In some embodiments, a disposable cap (not shown) can also be used to occlude a proximal end of a cuffless tracheostomy tube such that the patient breathes around the outer diameter of the tube and through the upper airway tract during the weaning process.

In some embodiments, disposable caps can be made available (e.g., sold) in a variety of sizes that correspond to various available cannula sizes of cuffless disposable cannula tracheostomy tubes and can be purchased separately.

Percutaneous

In some embodiments, the device can be used in conjunction with a percutaneous dilatational tracheotomy (P.D.T.) and can be inserted into the patient using, for example, an appropriate loading dilator provided with a percutaneous dilatational kit, such as, e.g., any appropriate kit known in the art. For example, a percutaneous kit can include, among other things, e.g., a rod-like introducer that is used to create a hole in a patient's neck.

In some percutaneous embodiments, an outer cannula includes a rigid tip, such as, e.g., a rigid percutaneous tip 70 similar to that shown in FIGS. 7-8. Additionally, while FIGS. 7-8 show a rigid tip 70 with a stepped portion, as should be understood based on the above, a stepped portion can be omitted in various embodiments.

Obturator

Figure 9:
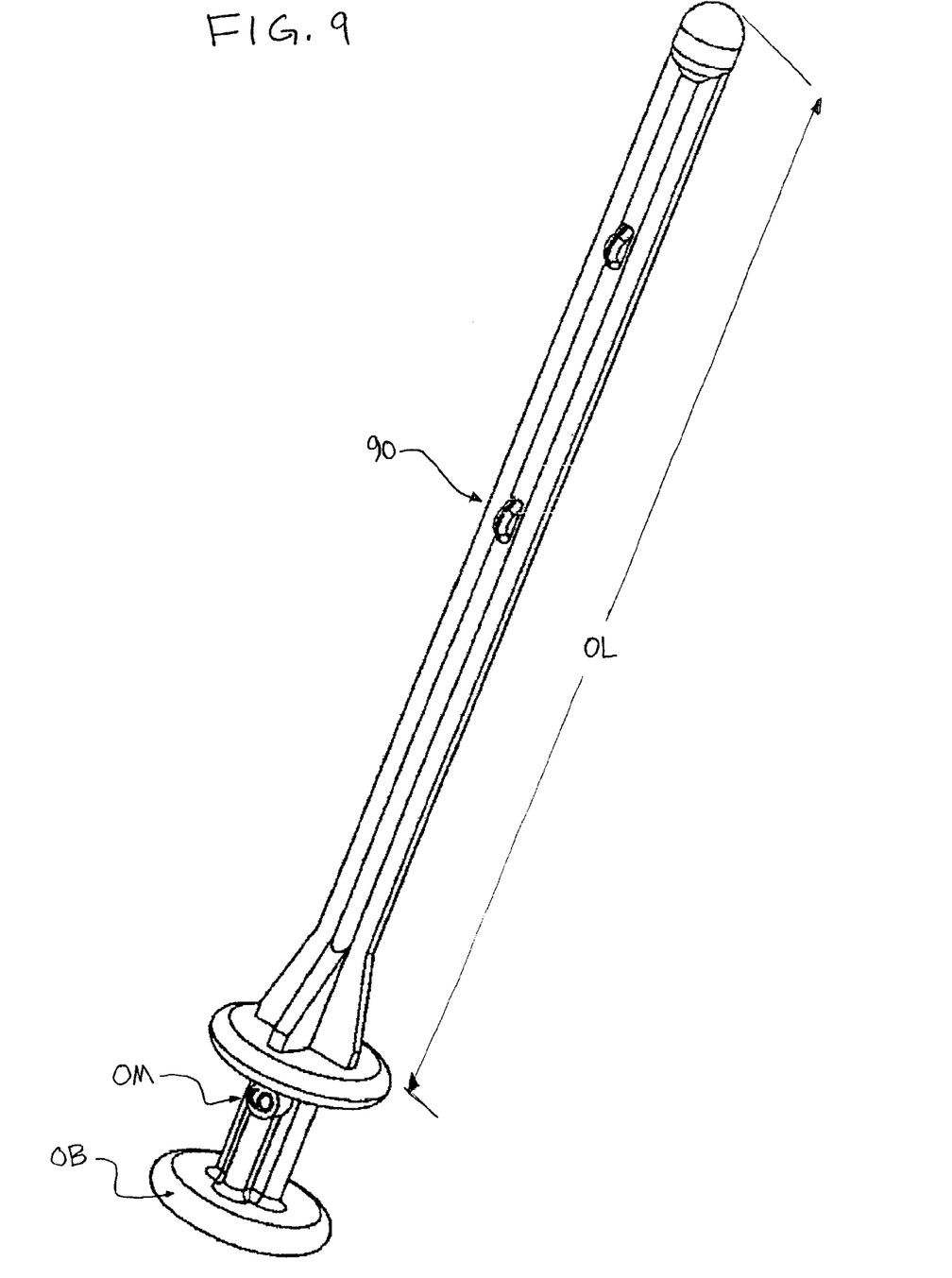
FIG. 9 is a perspective view of an obsturator according to some illustrative embodiments of the invention.

In some preferred embodiments, a tracheostomy tube assembly includes an obturator as shown in FIG. 9. An obturator can be used, e.g., to help insert the outer cannula into a patient in, e.g., non-percutaneous embodiments. For instance, the obturator can be initially inserted into the outer cannula during insertion and then removed. In some instances, an obturator can be stored in an accessible location near the patient for use during an unscheduled reintubation. Preferably, the obturator includes a smooth, rounded-tip that facilitates insertion. Preferably, the obturator is easy to insert and remove. Preferably, the obturator does not come out of the outer cannula in a manner to fall out under its own weight if the tube is in an inverted position. Preferably, the obturator does not recess into the outer cannula beyond its tolerance limit when insertion forces are applied to its distal tip while its proximal end is being held securely against the head assembly of the product. In some illustrative and non-limiting embodiments usable with products 6, 7, 8, 9, and 10 shown in FIG. 2, the obturator can have a length OL of about 3.866, 4.205, 4.345, 4.595, or 4.615 inches, respectively. In use, the physician can, e.g., grasp the obturator at the base OB. Preferably, the obturator includes an identification marking OM designating the size or other characteristics (e.g., a product size 6 being shown in the illustrated example).

In some illustrative embodiments, the obturator can be made with a high-density polyethylene (HDPE).

Other Features

In some embodiments, the tracheostomy tube system can also include some or all of the following additional features:

speaking and/or weaning means: such as, e.g., facilitating the administration of oxygen to be passed up the trachea across the vocal chords; and/or including fenestrations in the outer and/or inner cannula to facilitate speaking and/or weaning;

anti-microbial means: such as, e.g., an anti-microbial coating to reduce bacterial colonization;

evacuation means: such as an evacuation means (EVAC) that, e.g., facilitates the removal of, e.g., subglottic secretions which can pool above, e.g., a tube's cuff.

Illustrative Methods of Use (e.g., Surgical)

In some illustrative embodiments, methods of use can include at least some, preferably all, of the below-listed steps.

Step 1: Tube Insertion:

Initially, a physician can select an appropriate tracheostomy tube assembly size. Preferably, the obturator is inserted into the outer cannula. The obturator preferably is fully seated before the tube is inserted into the patient. In some instances, a thin film of water-soluble lubricant can be applied to the outer cannula, cuff and/or protruding portion of the obturator to facilitate insertion.

Before insertion, the physician will preferably perform a surgical or P.D.T. tracheotomy procedure. Then, the tracheostomy tube (i.e., the outer cannula) can be inserted into the patient's trachea with the obturator inside the tracheostomy tube. After the outer cannula is properly in place, the physician preferably removes the obturator promptly.

Then, the physician preferably inserts the disposable inner cannula into the outer cannula. Upon full insertion, the physician preferably locks the inner cannula in an inserted position by turning the inner cannula (such as, e.g., depicted in FIG. 1). For example, in some preferred embodiments, the inner cannula can be locked with two motions: 1) inserting the inner cannula to an insertion position; and 2) rotating the inner cannula to a locked position from the insertion position. Preferably, the inner cannula is locked upon a rotation of less than about 180 degrees, or, more preferably, less than about 135 degrees, or, more preferably, about 90 degrees or less. Preferably, the inner cannula is locked upon a rotation of between about between about 10 degrees to 170 degrees, or, more preferably, between about 45 degrees and 135 degrees, or, more preferably, between about 70 degrees and 110 degrees, or, more preferably, about ¼ turn or about 90 degrees. Preferably, the cannula locks in place upon a clockwise rotation and is released upon a counterclockwise rotation, such as, e.g., shown in FIG. 1.

Step 2: Cuff Inflation:

In embodiments having an inflatable cuff, the operation can be as follows. The cuff can preferably be inflated by injecting air into a luer valve of the inflation line using, for example, a hand-operated syringe (not shown).

Preferably, selection of cuff inflation and/or deflation procedures can be chosen at the discretion of the physician based on circumstances.

Step 3: Securement of Tube:

In some embodiments, the tracheostomy tube assembly can be secured to a patient using a neck strap. In preferred embodiments, a neck strap will be provided with an initial assembly kit.

Step 4: Cuff Deflation:

In some embodiments having an inflatable cuff, accumulated secretions above the cuff are evacuated by, e.g., suctioning before deflating the cuff, unless, e.g., suctioning is contraindicated.

Preferably, to deflate the cuff, the physician withdraws the air slowly from the luer valve of the inflation line using, e.g., a syringe (not shown).

Step 5. Using a Disposable Cap:

In some embodiments, a disposable cap (not shown) can be used. Preferably, the cap has a universal size that can be used with various model sizes. The cap preferably occludes the proximal end of the outer cannula, forcing the patient to breathe through the patient's upper airway tract. In this manner, this can help to establish the patency of the patient's upper airway tract. Preferably, the patient's airway is cleared by coughing and/or suctioning before capping the tracheostomy tube.

In some embodiments, to apply the cap, the physician pushes it securely over, e.g., a 15 mm connector.

In some embodiments, if a patient is to be mechanically ventilated, the cap can be removed, and the device can be connected to a ventilator.

Step 6. Removing the Inner Cannula:

In some embodiments, the inner cannula can be removed and/or replaced as follows. Preferably, the disposable inner cannula can be removed by manually rotating the inner cannula hub about ¼ turn counterclockwise (such as, e.g., shown in FIG. 1) and, then, manually pulling it outward.

Preferably, after the inner cannula has been removed, it can be replaced with a new inner cannula. If desired, a ventilator can then be connected to provide or reestablish ventilation. In embodiments having an inflatable cuff, before removing the outer cannula tracheostomy tube, the cuff is preferably substantially completely deflated (such as, e.g., using a syringe). This can help to ensure, e.g., that the cuff passes through the stoma with minimal resistance.

Illustrative Percutaneous Methods

In some embodiments, the device can be configured for percutaneous use. In this regard, for example, the tracheostomy tube can be used, e.g., in conjunction with P.D.T. Accordingly, sterile techniques can be followed for the handling and placement of the tracheostomy tube.

In some illustrative embodiments, methods of use can include at least some, preferably all, of the below-described steps.

In some embodiments, a tracheostomy tube loading dilator can be inserted into the outer cannula such that a tapered section of the loading dilator clears the distal tip of the tracheostomy tube (such as, e.g., by a few centimeters). In some instances, a film of water-soluble lubricant can be applied to the outer cannula, a cuff (when present) and a protruding portion of loading dilator to facilitate insertion. As discussed above, a tracheostomy tube loading dilator is part of a percutaneous dilatational kit as known in the art. The physician can then perform the dilatational tracheotomy procedure and can insert the tracheostomy tube in accordance with the P.D.T. procedure.

After the physician verifies a secure airway, the physician preferably inserts and locks the inner cannula. In some embodiments, a breathing apparatus can be attached to the tracheostomy tube and the cuff can be inflated as set forth below.

In preferred embodiments, using aseptic non-contaminating techniques, the inner cannula can be inserted into position. In some instances, the inner cannula can be moistened with, e.g., sterile saline to facilitate insertion.

Broad Scope of the Invention

While illustrative embodiments of the invention have been described herein, the present invention is not limited to the various preferred embodiments described herein, but includes any and all embodiments having modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." Means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited.

What is claimed is:

1. A multiple cannula assembly for insertion into a patient, comprising:
   a) a flexible outer cannula having a head including a connector and at least one ridge and at least one stop portion, said outer cannula having a substantially rigid tip including a stepped portion configured to reduce an outward bulge of a cuff;
   b) a flexible inner cannula having a hub including at least one protrusion engageable with said at least one ridge of said outer cannula head;
   c) said inner cannula being longitudinally insertable into said outer cannula to an insertion position in which said inner cannula hub is positioned at least partially within said outer cannula head; and d) said inner cannula hub being rotatable relative to said outer cannula head in a locking direction from said insertion position to a locked position in which said at least one protrusion of said hub is engaged with said at least one ridge of said head, said at least one stop portion inhibiting rotation of said inner cannula hub in said locking direction beyond said locked position of said inner cannula hub.

2. The assembly of claim 1, wherein said at least one protrusion is locked with said at least one ridge upon rotation of said hub between about 70 degrees and 110 degrees from said insertion position of said inner cannula.

3. The assembly of claim 2, wherein said at least one protrusion is locked with said at least one ridge upon rotation of said hub about ¼ turn clockwise from said insertion position of said inner cannula.

4. The assembly of claim 1, wherein said cuff is expandable.

5. The assembly of claim 1, wherein said outer cannula includes a percutaneous tip.

6. The assembly of claim 1, wherein said substantially rigid tip portion of said outer cannula is fixed to a substantially flexible portion.

7. The assembly of claim 6, wherein said substantially rigid tip is RF welded to said substantially flexible portion.

8. The assembly of claim 1, wherein said outer cannula head includes a connector configured to connect to respiratory equipment in said locked position.

9. The assembly of claim 8, wherein said connector of said outer cannula head is a 15 mm connector.

10. The assembly of claim 1, wherein said inner cannula hub includes a knurled portion that extends from said outer cannula head when said inner cannula hub is in said locked position.

11. The assembly of claim 10, wherein a diameter of said knurled portion is smaller than a diameter of said connector.

12. The assembly of claim 1, wherein said assembly is a tracheostomy tube assembly.

13. The assembly of claim 1, wherein said hub is overmolded to said inner cannula.

14. The assembly of claim 1, wherein the cuff is inflatable and the assembly includes a cuff pressure indicator.

15. The assembly of claim 1, wherein said inner cannula comprises a PTFE material.

16. A multiple cannula assembly for insertion into a patient, comprising:

a) a flexible outer cannula having a head including a connector and at least one ridge, said outer cannula having a substantially rigid tip including a stepped portion configured to reduce an outward bulge of a cuff;

b) a flexible inner cannula having a hub including at least one protrusion engageable with said at least one ridge of said outer cannula head, wherein said inner cannula comprises a material having fibers oriented along a length of said inner cannula and nodes around a circumference of said inner cannula;

c) said inner cannula being longitudinally insertable into said outer cannula to an insertion position in which said inner cannula hub is positioned at least partially within said outer cannula head; and d) said inner cannula hub being rotatable relative to said outer cannula head from said insertion position to a locked position in which said at least one protrusion of said hub is engaged with said at least one ridge of said head.

17. The assembly of claim 16, wherein said outer cannula includes a substantially flexible portion coupled to said substantially rigid tip portion.

18. The assembly of claim 17, wherein:

said substantially rigid tip portion of said outer cannula is formed of a rigid PVC material having a shore D hardness of between about 55 to 65; and said substantially flexible portion of said outer cannula is formed of a flexible PVC material having a shore A hardness of between about 80 to 90.

19. A method for using an insertable multiple cannula assembly, the method comprising:

positioning a flexible inner cannula in an insertion position within a flexible outer cannula such that a hub of said inner cannula is positioned at least partially within a head of said outer cannula, said outer cannula having a substantially rigid tip including a stepped portion;

rotating said hub of said inner cannula relative to said head of said outer cannula in a locking direction from said insertion position to a locked position in which at least one protrusion of said hub is engaged with at least one ridge of said head, wherein at least one stop portion inhibits rotation of said inner cannula hub in said locking direction beyond said locked position of said inner cannula hub; and inflating a cuff coupled to said outer cannula, wherein the stepped portion of the outer cannula tip reduces an outward bulge of the inflated cuff.

20. An outer cannula for use in a multiple cannula assembly for insertion into a patient, the outer cannula comprising:

a flexible body;

an inflatable cuff having at least one end secured to the flexible body; and a substantially rigid tip coupled to the flexible body portion, the substantially rigid tip including a stepped portion configured to reduce an outward bulge of the inflatable cuff.

* * * * *